(12) United States Patent
Swihart et al.

(10) Patent No.: US 9,736,388 B2
(45) Date of Patent: Aug. 15, 2017

(54) NON-DESTRUCTIVE READ OPERATIONS WITH DYNAMICALLY GROWING IMAGES

(71) Applicant: Bio-Rad Laboratories, Inc., Hercules, CA (US)

(72) Inventors: Steve Swihart, Walnut Creek, CA (US); Evan Thrush, San Anselmo, CA (US); Boaz Ran, Haifa (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 253 days.

(21) Appl. No.: 14/563,355

(22) Filed: Dec. 8, 2014

(65) Prior Publication Data

US 2015/0172526 A1    Jun. 18, 2015

Related U.S. Application Data

(60) Provisional application No. 61/915,930, filed on Dec. 13, 2013.

(51) Int. Cl.
*H04N 7/12* (2006.01)
*H04N 11/04* (2006.01)
(Continued)

(52) U.S. Cl.
CPC ......... *H04N 5/2353* (2013.01); *G01N 21/272* (2013.01); *G01N 21/6408* (2013.01);
(Continued)

(58) Field of Classification Search
None
See application file for complete search history.

(56) References Cited

U.S. PATENT DOCUMENTS 7,163,822 B2   1/2007   Yazawa et al.
8,310,577 B1 *  11/2012  Neter .................. H04N 5/365
                                                  348/308
(Continued)

FOREIGN PATENT DOCUMENTS

DE      10146902 A1    9/2002
EP       2226762 A1    9/2010
(Continued)

OTHER PUBLICATIONS

Search Report, dated Apr. 15, 2015, for International Patent Application PCT/US2014/069359, 4 pages.
(Continued)

*Primary Examiner* — Talha M Nawaz
(74) *Attorney, Agent, or Firm* — Kilpatrick Townsend and Stockton LLP

(57) ABSTRACT

Methods and digital imaging devices disclosed herein are adapted to capture images of a specimen in a chemical reaction using a series of short exposures of light emissions from the specimen over a period of time. The series of short exposures is captured using an array of pixels of an image sensor in the digital imaging device that are configured for performing continuous non-destructive read operations to read out a set of non-destructive read images of the specimen from the pixel array. In one embodiment, images are captured by delaying the read out until at or near the end of the chemical reaction to reduce read noise in the images. The signals read out from the image sensor can be continuously monitored and the capturing of images can be discontinued either automatically or based on a command from a user. The captured images can then be displayed in a graphical display.

19 Claims, 14 Drawing Sheets

(51) Int. Cl.

| | |
|---|---|
| *H04N 11/02* | (2006.01) |
| *H04N 5/235* | (2006.01) |
| *H04N 5/361* | (2011.01) |
| *H04N 5/217* | (2011.01) |
| *H04N 5/355* | (2011.01) |
| *G01N 21/76* | (2006.01) |
| *G01N 21/27* | (2006.01) |
| *G01N 21/64* | (2006.01) |

(52) U.S. Cl.
CPC ......... *G01N 21/6456* (2013.01); *G01N 21/76* (2013.01); *H04N 5/2173* (2013.01); *H04N 5/2355* (2013.01); *H04N 5/35545* (2013.01); *H04N 5/361* (2013.01)

(56) References Cited

U.S. PATENT DOCUMENTS

| | | | |
|---|---|---|---|
| 2002/0050518 A1 | 5/2002 | Roustaei | |
| 2003/0157581 A1* | 8/2003 | Grill | C12Q 1/6837 435/8 |
| 2003/0219891 A1 | 11/2003 | Yazawa | |
| 2004/0219602 A1 | 11/2004 | Carlson et al. | |
| 2005/0266603 A1* | 12/2005 | Findlater | H01L 27/14621 438/69 |
| 2007/0268396 A1* | 11/2007 | Kurane | H04N 5/2353 348/362 |
| 2008/0007645 A1* | 1/2008 | McCutchen | H04N 5/238 348/360 |
| 2009/0015831 A1* | 1/2009 | Yguerabide | C12Q 1/6816 356/337 |
| 2011/0090332 A1 | 4/2011 | Hing | |
| 2013/0076951 A1 | 3/2013 | Endo | |

FOREIGN PATENT DOCUMENTS

| | | |
|---|---|---|
| WO | 98/46007 A1 | 10/1998 |
| WO | 2008027840 A1 | 3/2008 |
| WO | 2008103865 A2 | 8/2008 |
| WO | 2013138646 A1 | 9/2013 |

OTHER PUBLICATIONS

Written opinion, dated Apr. 15, 2015, for International Patent Application PCT/US2014/069359, 7 pages.
Bosco, A. et al., "A Temporal Noise Reduction Filter Based on Image Sensor Full-Frame Data", Consumer Electronics, 2003. ICCE. 2003 IEEE International Conference on Consumer Electronics (Jun. 17-19, 2003), pp. 402-403.
Esposito, M. et al., "CMOS APS in pre-clinical science: next generation disruptive technology for multi-modality imaging", presented IEEE Nuclear Science Symposium and Medical Imaging Conference, Anaheim, CA, (Nov. 2012), 4 pages.
Esposito, M. et al., "Using a large area CMOS APS for direct chemiluminescence detection in Western Blotting Electrophoresis", presented SPIE Medical Imaging Conference, San Diego, CA, (Feb. 2012), 8 pages.
"Innovation Flyer" for Image Senser Design & Innovation, DynAMITe- Wor;d's Largest Radiation-hard CMOS Imager, downloaded from URL: http://www.isdicmos.com/downloads/isdi_flyer.pdf, 2 pages.
Rudolph, M. et al., "Time Course for MuiGLO® HRP Chemiluminescent Substrates on Nitrocellulose Membrane", KPL, Inc. (2013), 4 pages.
Search Report, dated Feb. 12, 2015, for International Patent Application PCT/US2014/069359, 2 pages.
Unpublished US Patent Application, naming Ran et al., filed Dec. 8, 2014 for U.S. Appl. No. 14/563,411, 38 pages.
Search Report, dated Mar. 10, 2015, for International Patent Application PCT/US2014/069281, 1 page.
Written Opinion, dated Mar. 10, 2015, for International Patent Application PCT/US2014/069281, 5 pages.
Supplementary European Search Report mailed Nov. 2, 2016 in EP 14869552, 7 pages.
Radspinner, David. A. et al.; "The revolutionary impact of today's array detector technology on chemical analysis"; International Conference on Scientific Optical Imaging (1990); SPIE vol. 1439; pp. 2-14.
Extended European Search Report dated Nov. 18, 2016 in EP Patent Application No. 14869916.8. 10 pages.

* cited by examiner

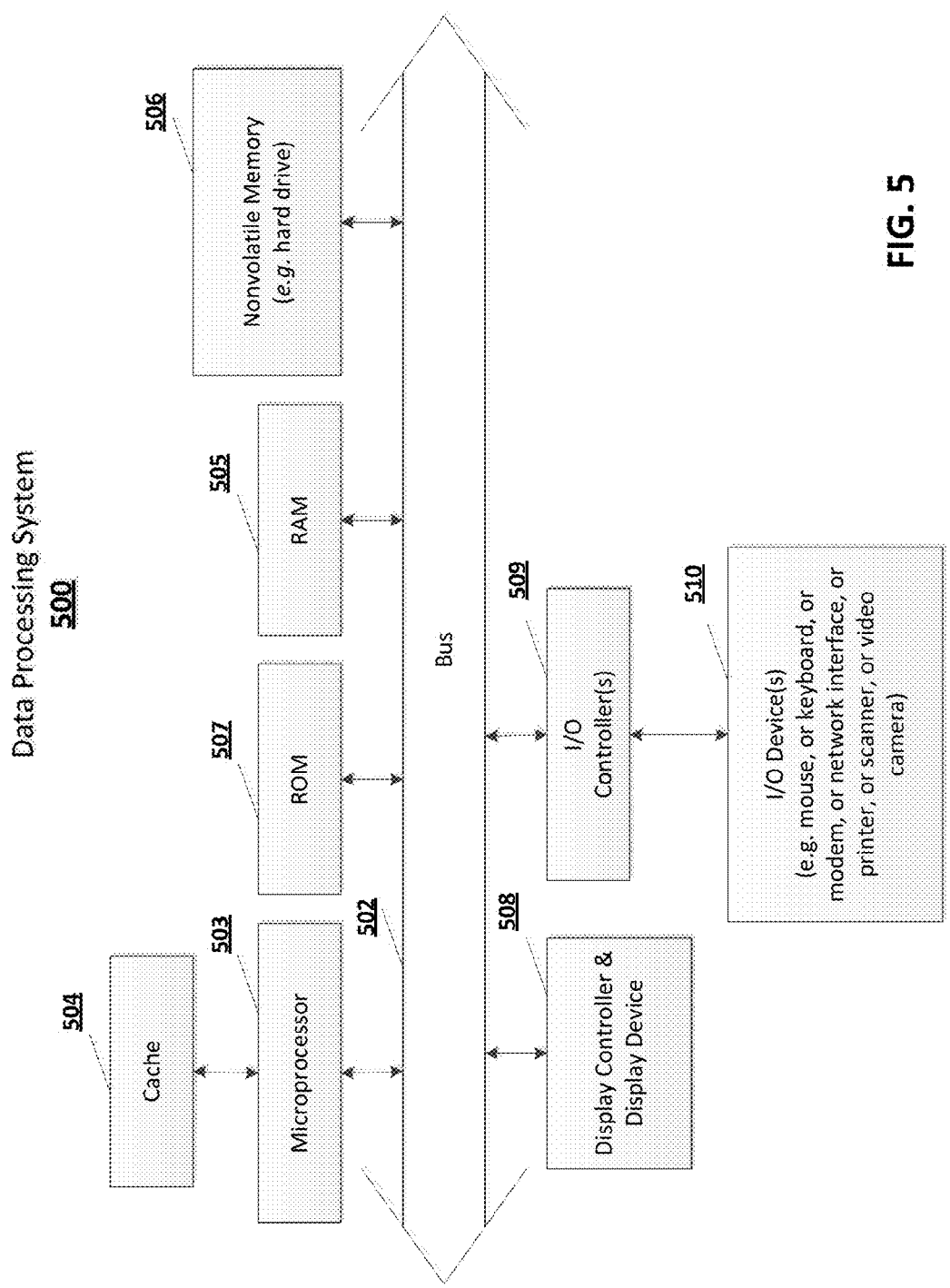

NON-DESTRUCTIVE READ OPERATIONS WITH DYNAMICALLY GROWING IMAGES

CROSS-REFERENCES TO RELATED APPLICATIONS

This application is a nonprovisional of and claims the benefit of priority of U.S. Provisional Application No. 61/915,930, titled, "Non-Destructive Read Operations With Dynamically Growing Images," filed on Dec. 13, 2013, which is herein incorporated by reference it its entirety for all purposes.

FIELD OF THE INVENTION

The embodiments described herein relate generally to capturing images of specimens in chemical reactions. More particularly, embodiments relate to capturing images of specimens in chemical reactions using non-destructive read operations in a digital imaging device.

BACKGROUND OF THE INVENTION

Capturing images of light or other (including radiological) signals emitted from specimens during a chemical reaction has been used to determine the components of a specimen based on where spatially separated bands or regions of light are emitted from the specimen. Certain components of a specimen may emit light in brighter bands of light requiring shorter exposure times for image capture while other constituents may emit light in dimmer bands requiring longer exposure times. Problems can arise when "read noise" occurs during image capture and distorts the captured image, particularly for specimen components that emit light in weakly emitting bands.

In order to overcome read noise limitations for weak samples, it is common to integrate or collect the charge over a long exposure of the CCD or CMOS. The long exposures do not allow the measurement system to measure the signal in continuous-like fashion. In other works, one could take many shorter images, but the system would not be very sensitive because read noise would be introduced with each short exposure. If you sum the short exposure, this helps reduce the read noise some but it is still not as sensitive as conducting one long exposure using a conventional image sensor. In this case of image summing, the read noise is known to increase in captured images as the square root of the number of exposures.

Many trained artisans in the field have therefore struggled with solving the problem of monitoring weak chemical reactions in a continuous-like manner while maintaining high sensitivity. As discuss below, there a several key advantages to method that would allow fast monitoring of chemical reactions while not compromising sensitivity.

BRIEF SUMMARY OF THE INVENTION

Techniques for capturing images of a specimen in a chemical reaction using a digital imaging device are described herein. At least certain embodiments are adapted to capture a series of short exposures of light emissions from the specimen over a period of time using an array of pixels of an image sensor in the digital imaging device. The images are captured by performing continuous non-destructive read operations to read out a set of non-destructive read images of the specimen from the pixel array. In one embodiment, images are captured by delaying the read out of the set of signals until at or near the end of the chemical reaction to reduce read noise in the images.

The signals read out from the image sensor can be monitored and the capturing of the images can be discontinued automatically or upon occurrence of a predetermined event such as receiving a command from a user of the digital imaging device. The captured images can then be displayed in a graphical display.

One advantage of the techniques introduced herein is that almost no read noise is introduced by capturing the series of short exposures using the non-destructive read operations. These and other embodiments along with many of their advantages and features are described in more detail in conjunction with the description below and attached figures.

BRIEF DESCRIPTION OF THE DRAWINGS

FIG. 5 depicts an example block diagram of a data processing system upon which the disclosed embodiments may be implemented.

DETAILED DESCRIPTION OF THE INVENTION

Figure 1A:
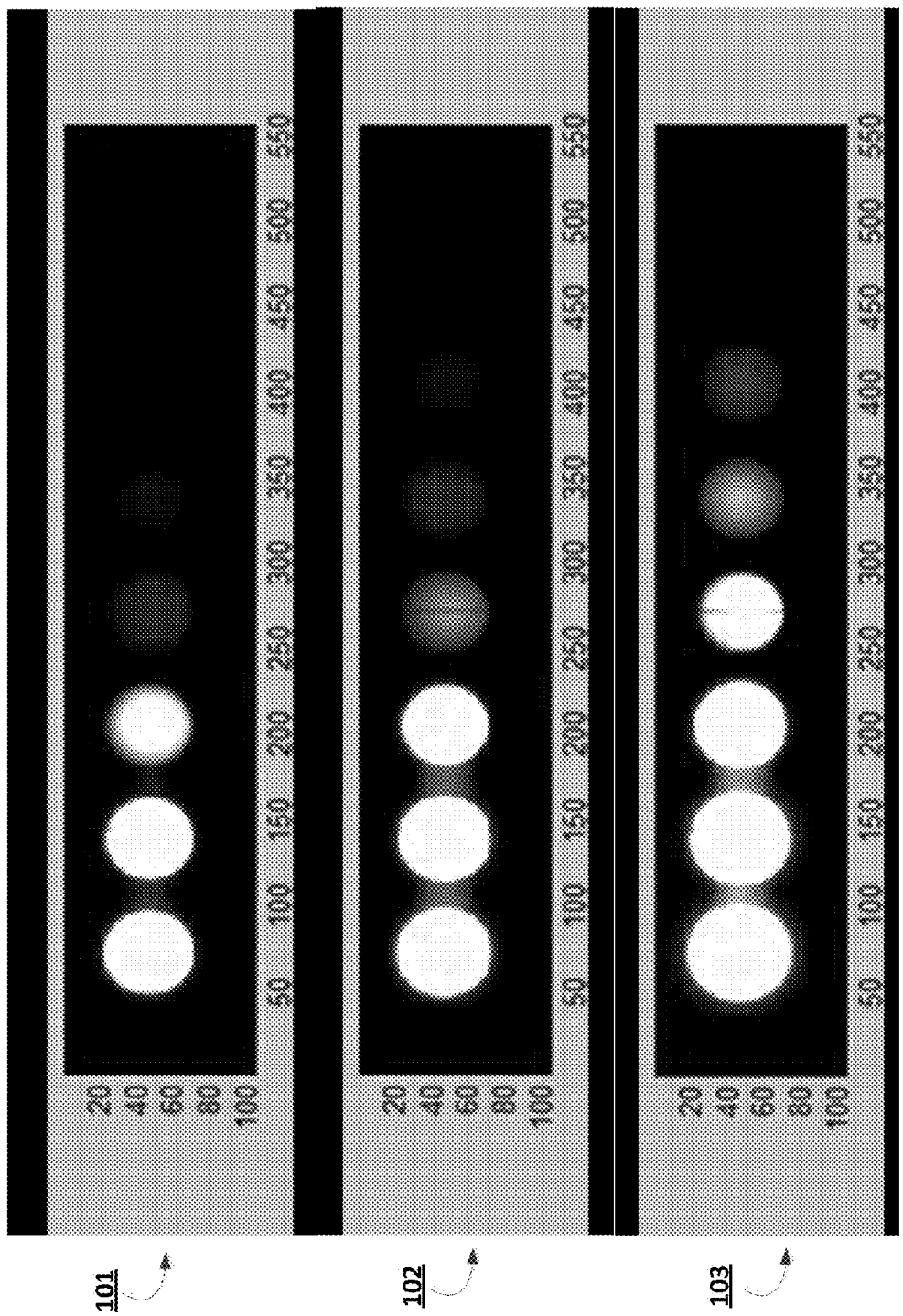
FIG. 1A depicts a graphical representation of an image of a specimen in a chemiluminescence reaction captured using a series non-destructive read operations according to one example embodiment.

Throughout this description for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form to avoid obscuring the underlying principles of the described embodiments.

The methods and digital imaging devices introduced herein are adapted to capture images of a specimen in a chemical reaction using a series of short exposures of light emissions from the specimen over a period of time during a chemical reaction where the captured images grow dynamically over the time period as the number of exposures increases. For example, in some embodiments, the specimen can be bound to a blotting membrane and the light emissions or other (e.g., radiological) signals are emitted directly or indirectly by a probe.

The series of short exposures is captured using an array of pixels of an image sensor in the digital imaging device configured for performing continuous non-destructive read operations. Non-destructive read operations read out a set of electrical signals representing non-destructive read images of the specimen from the pixel array. The set of signals are generated from charge stored in the pixel array. In one embodiment, images are captured by delaying the read out of the set of signals until at or near the end of the chemical reaction to reduce read noise in the images. Taking multiple images using non-destructive read operations can reduce read noise so there is little penalty to taking multiple images and monitoring the signal in a continuous like manner.

Embodiments are further configured to continuously monitor the signals read out from the image sensor and to discontinue capturing images of the specimen upon a predetermined event such as receiving a command. In one embodiment the commands can be generated automatically. In other embodiments, the commands can be based on input from a user of the digital imaging device. The captured images can then be displayed in a graphical display. Embodiments described herein are configured to capture images of specimens in chemical reactions. The chemical reactions can, for instance, include chemiluminescence reactions, fluorescence reactions, or absorbance reactions. Other types of reactions are possible.

In a preferred embodiment, the digital imaging device is a complementary metal-oxide-semiconductor ("CMOS") digital imaging device capable of performing non-destructive read operations. CMOS digital imaging devices exhibit minimal blooming due to over-saturation of bright pixels. Long exposures of bright bands of light emitted from the specimen can be performed even if the bright bands are located in proximity to faint bands emitted from the specimen. But other digital imaging devices may also be used.

Further, the dynamic range of the captured images of the specimen can be increased by combining data from shorter-time read images of the set of non-destructive read images for brighter areas of the specimen with data from longer-time read images of the set of non-destructive read images for dimmer areas of the specimen. Combining the read data from shorter-time non-destructive read images with read data from longer-time non-destructive read images only requires data from a single measurement or non-destructive read exposure sequence.

Emission profiles of multiple different assays can also be obtained and stored in the memory of the digital imaging device. The emissions profiled include information relating to when an emission for a particular specimen will begin rapidly declining. The emission profile data is either known beforehand or can be measured by a user.

The emission profile data can be used to improve autoexposure of the particular specimen. Further, signals for bright bands can be determined by expanding the bit depth of the captured digital image and calculating the signals for the bright bands based on a ratio of the exposure time of the specimen taken by the digital imaging device to the total exposure time obtained from emission profile data. The emission profile data can also be used as a basis for querying the user of the digital imaging device when an emission of a specimen is at or near its peak to determine if the user wants to discontinue capturing images of the specimen. Different weights can also be assigned to different frames of the series of non-destructive read images based on the emission profile data.

In one embodiment, images of the specimen can be captured at a high frame rate using the non-destructive read operations and averaged at the end of the capture period to remove read noise. For instance, the frames can be captured only when intensity is stable enough based on the emission profile data. Each signal read out from the image sensor can be averaged as a function of time to estimate the amount of signal present to increase sensitivity of the image sensor. The intensity of each signal read out from the image sensor can then be calculated based on its location in the array of pixels in cases where the time profile of the signals is location dependent. The signals can then be shifted in location to the same time instance as if each of the signals started simultaneously at each location. This can be done to improve repeatability of the images captured by the digital imaging device.

Other embodiments are adapted to measure the time profile of the light emitted from the specimen using the non-destructive read images as well as the time profile of background regions close to one or more bands of interest in the captured image. The light emitted from the specimen can then be discriminated from the background regions using a temporal difference between the two time profiles. This can be done to improve sensitivity and repeatability of the image sensor and enable better discrimination of any unwanted background noise from the signals read out from the image sensor.

In addition, black pixels in the background regions can be utilized to measure dark current noise. Dark current is the relatively small electric current that flows through photosensitive devices even when no photons are entering the device. Dark current is one of the main sources for noise in image sensors such as charge-coupled devices. Physically, dark current is due to the random generation of electrons and holes within the depletion region of the device that are then swept by the high electric field. The dark current noise can be measured dynamically for each exposure and to eliminate local offsets and gain variations arising from temperature variations based on the dark current noise measurements. The pattern of different dark currents can result in a fixed-pattern noise. Fixed pattern dark noise reduction within the captured image can be improved based on the dark current noise measurements.

Imaging arrays are used to produce an image representing an object. The imaging arrays are typically formed from rows and columns of photodetectors which generate photo-charges proportional to light reflected from the object to be imaged. The photo-charges from each pixel are converted to a signal (charge signal) or a potential representative of the level of energy reflected from a respective portion of the object and the signal or potential is read and processed by video processing circuitry to create the image. The output nodes of pixels in the same column are usually commonly connected and each pixel in the column is individually controlled to read-out at the common output node.

In non-destructive reads, the light information is continuously stored in the imaging device even during the read out process. FIG. 1A depicts a graphical representation of an image of a specimen in a chemiluminescence reaction captured using a series non-destructive read operations according to one example embodiment. Chemiluminescence is the emission of light (luminescence), as the result of a chemical reaction. There may also be limited emission of heat. Chemiluminescence differs from fluorescence in that the electronic excited state is derived from the product of a chemical reaction rather than the more typical way of creating electronic excited states, namely absorption. It is the antithesis of a photochemical reaction, in which light is used to drive an endothermic chemical reaction. In chemiluminescence, light is generated from a chemically exothermic reaction.

Figure 1B:
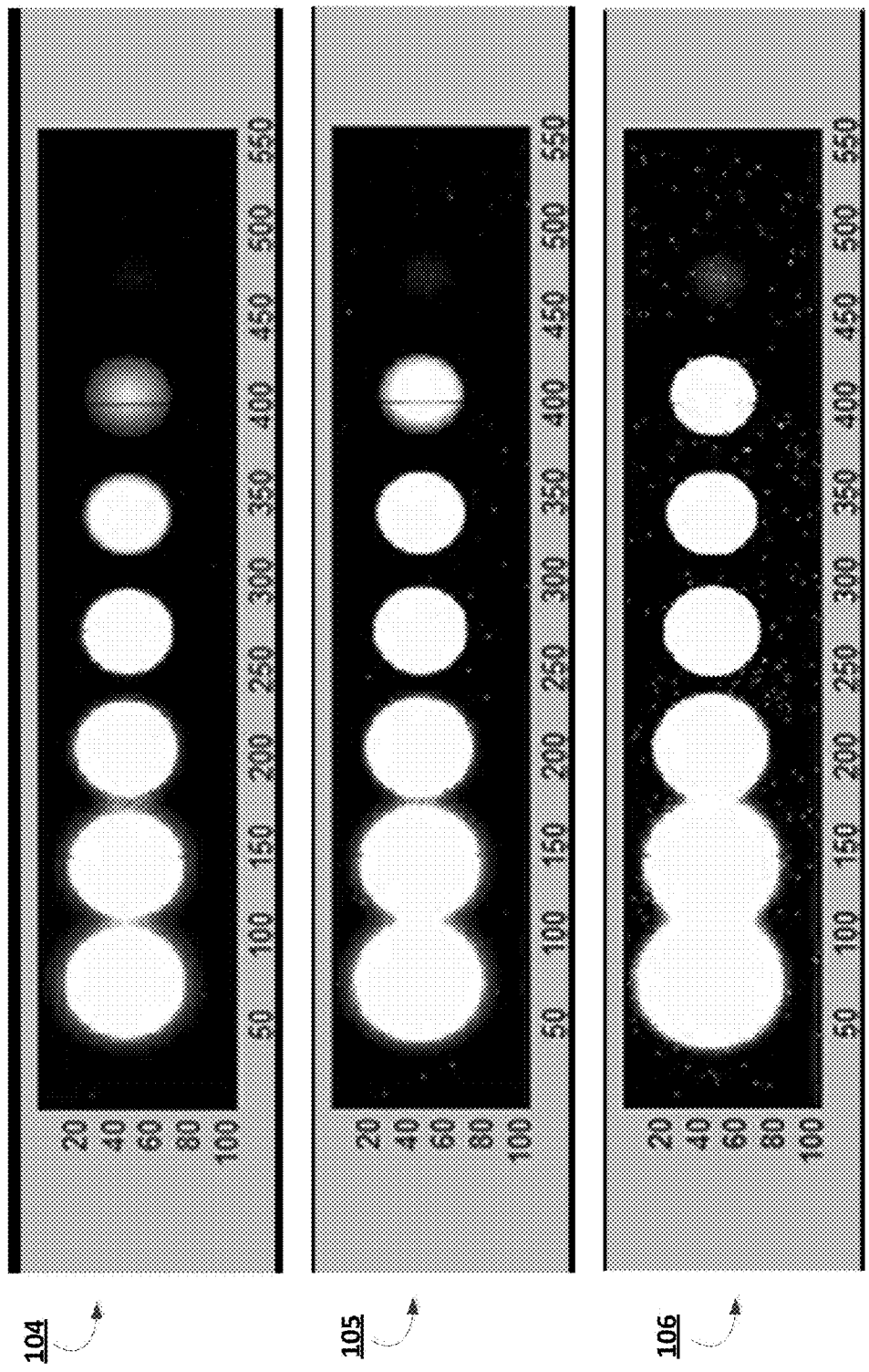
FIG. 1B depicts a further graphical representation of an image of a specimen in a chemiluminescence reaction captured using a series non-destructive read operations according to one example embodiment.

In the illustrated embodiment, the image captured grows dynamically at each time increment 101, 102, and 103 as the number of exposures increases over the image capture time period. As can be seen, the images captured of the bright bands shows significant detail while the faint bands are still growing. FIG. 1B depicts a further graphical representation of an image of a specimen in a chemiluminescence reaction captured using a series non-destructive read operations. In this depiction, the distortion on the brighter bands from read noise worsens with each time increment 104, 105 and 106 as the number of exposures increases over the image capture time period. But at these later times, the detail of the images of the faint bands has increased from the earlier images. This leads to problems in capturing high-quality images for components that emit light in dimmer bands of a specimen in a chemical reaction while minimizing the distortion for images of components that emit light in brighter bands.

Figure 2:
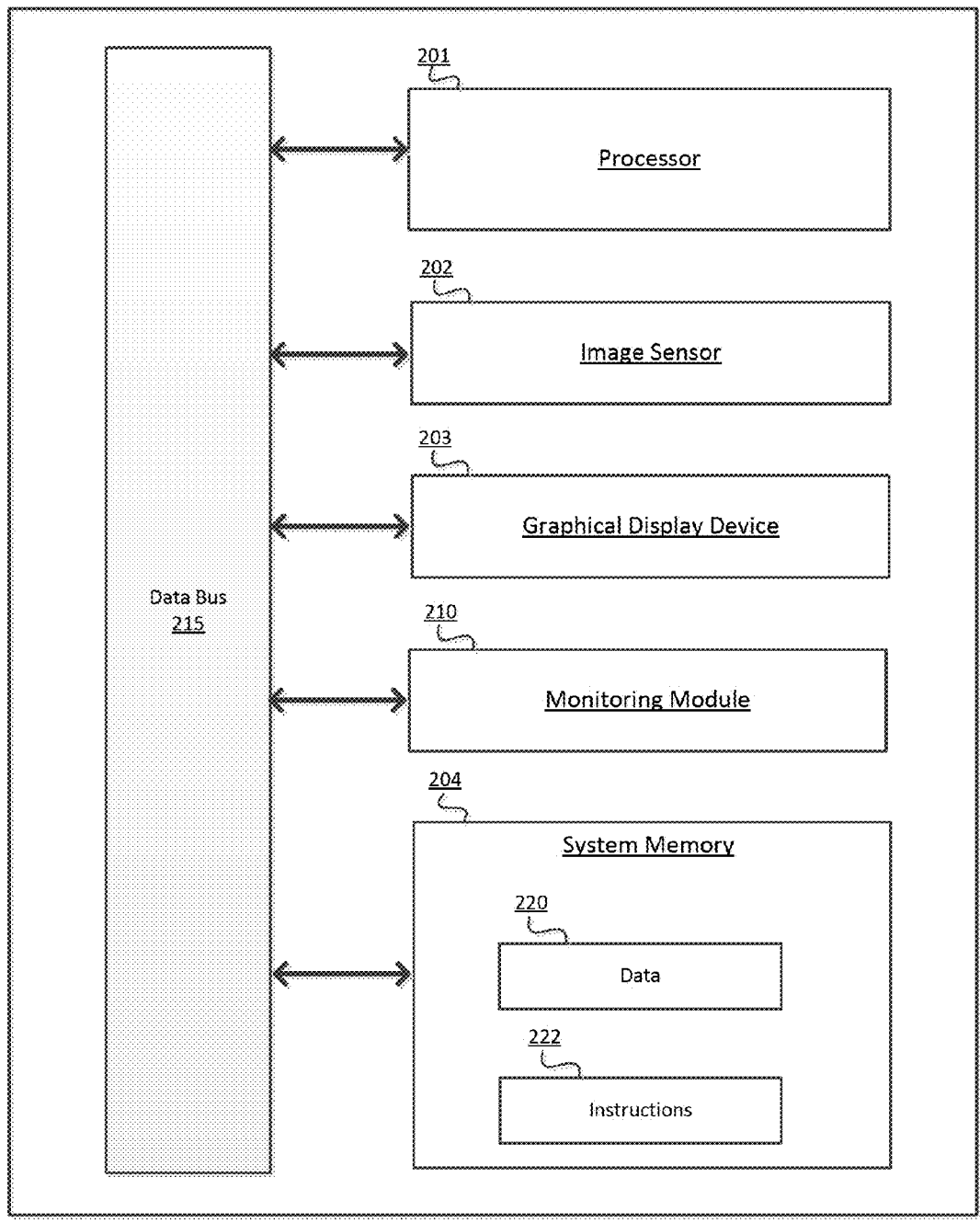
FIG. 2 depicts an example block diagram of digital imaging device for capturing an image of a specimen in a chemiluminescence reaction using a series non-destructive read operations according to one embodiment.

FIG. 2 depicts an example block diagram of digital imaging device for capturing an image of a specimen in a chemiluminescence reaction using a series non-destructive read operations according to one embodiment. In the illustrated embodiment, digital imaging device 200 includes a processor 201 and a system memory 204 coupled together via data bus 215. For the purposes of the present disclosure, processor 201 can be any processor known in the art including a microprocessor or microcontroller of any sort that is capable of executing instructions to perform operations. Likewise, system memory 204 can be any type of memory known in the art that is capable of storing data (220) and instructions (222) such as a random access memory (RAM), read-only memory (ROM), or other volatile or nonvolatile memories, etc.

Digital imaging device 200 further includes an image sensor 202 coupled with data bus 215. An image sensor is a device that converts an optical image into an electronic signal. It is used mostly in digital cameras, camera modules and other imaging devices. Most currently used image sensors are digital charge-coupled devices ("CCDs") or complementary metal-oxide-semiconductor ("CMOS") active pixel sensors. Image sensor 202 includes an array of pixels for capturing a series of short exposures of light emissions from a specimen over a period of time during a chemical reaction. Image sensor 202 can be configured to perform continuous non-destructive read operations to read out a set of signals representing non-destructive read images of the specimen from the array of pixels by delaying the reading out the signals until the end of the time period to reduce read noise in the set of non-destructive read image signals.

Digital imaging device 200 further includes a monitoring module 210 coupled with the data bus 215. Monitoring module 210 can be configured in certain embodiments to continuously monitor signals read out from the image sensor and discontinue capturing images of the specimen either automatically or based on input from a user of the digital imaging device. Digital imaging device 200 further includes a graphical display device 203 to display the captured images of the specimen.

Figure 3A:
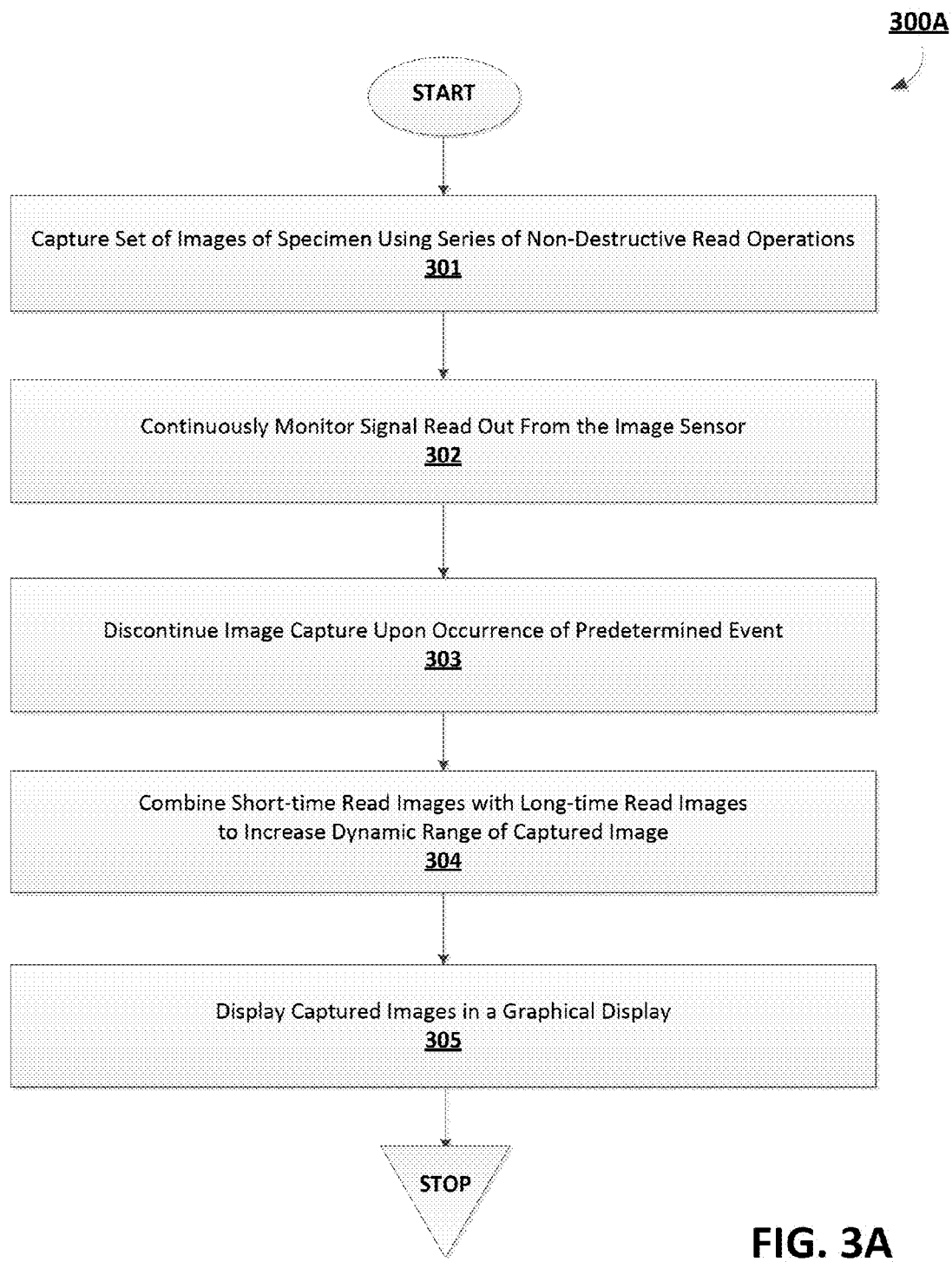
FIG. 3A depicts an example flow chart of a process of capturing an image of a specimen in a chemiluminescence reaction using a series non-destructive read operations according to one embodiment.

FIG. 3A depicts an example flow chart of a process of capturing an image of a specimen in a chemiluminescence reaction using a series non-destructive read operations according to one embodiment. In the illustrated embodiment, process 300A begins at operation 301 where a series of short exposures of light emissions from the specimen is captured over a period of time during the reaction using a series of non-destructive read operations to read out a set of signals representing non-destructive read images of the specimen from the array of pixels of the image sensor. In one embodiment, the reading out of the set of signals is delayed until the end of the time period to reduce read noise in the set of non-destructive read images.

Process 300A continues by continuously monitoring the set of signals read out from the image sensor (operation 302) and discontinuing capturing images of the specimen upon occurrence of a predetermined event (operation 303). In one embodiment, the image capture can be discontinued automatically. In other embodiments, the predetermined event includes receiving a command from a user of the digital imaging device. Other predetermined events are possible.

The dynamic range of the captured images of the specimen can then be increased by combining data from shorter-time read images for brighter areas of the specimen with data from longer-time read images for dimmer areas of the specimen (operation 304). The captured images of the specimen can then be displayed in a graphical display (operation 305). This completes process 300A according to one example embodiment.

Figure 3B:
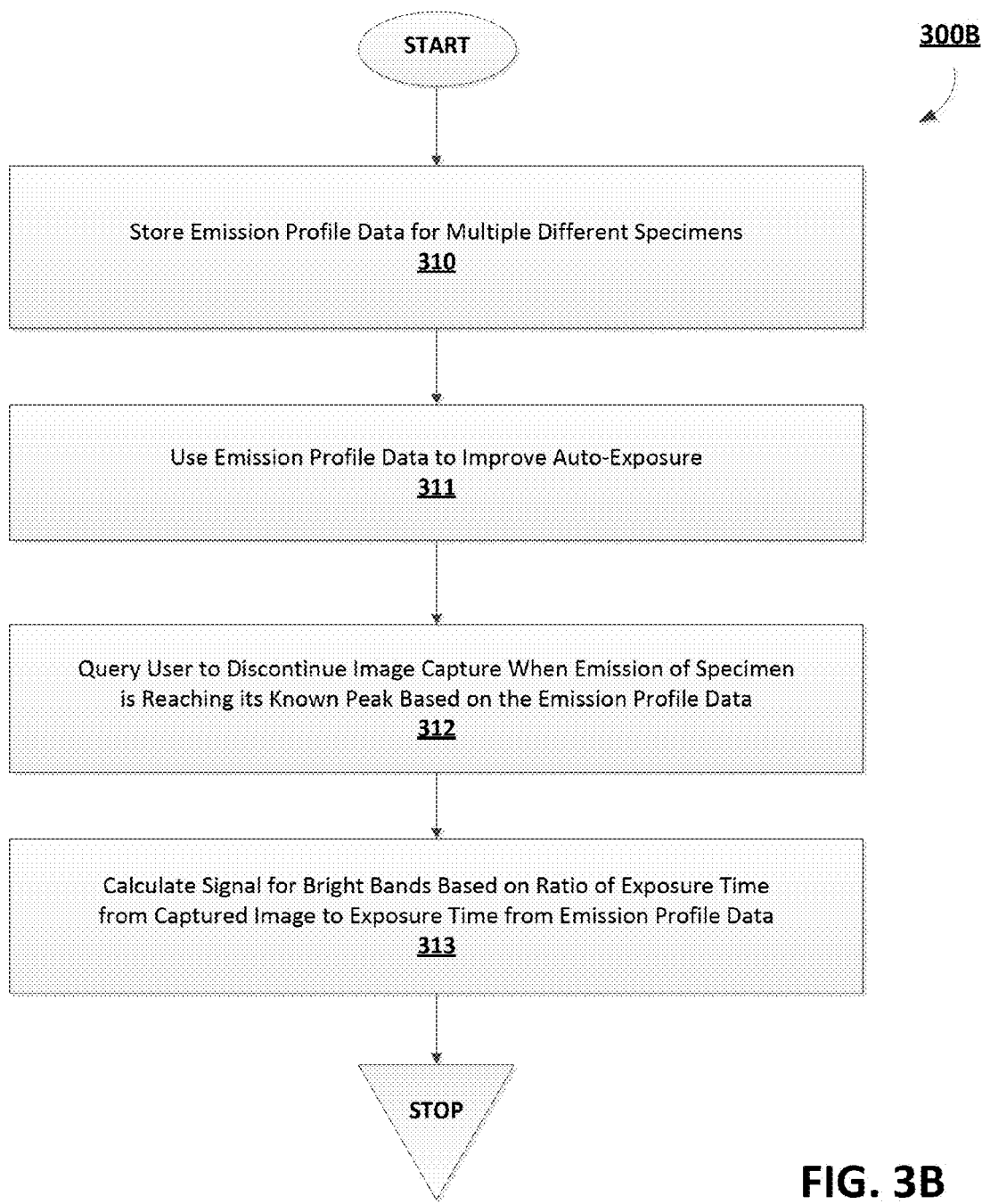
FIG. 3B depicts an example flow chart of a process of using known emission profile data to capture an image of a specimen in a chemiluminescence reaction using a series non-destructive read operations according to one embodiment.

FIG. 3B depicts an example flow chart of a process of using known emission profile data to capture an image of a specimen in a chemiluminescence reaction using a series non-destructive read operations according to one embodiment. In the illustrated embodiment, process 300B begins at operation 310 by storing in memory of the digital device emission profile data of multiple different assays including information relating to when an emission for a particular assay will begin rapidly declining. The emission profile data can either be known beforehand or measured by a user of the digital imaging device.

In one embodiment, the emission profile data is used to improve auto-exposure of the particular specimen at operation 311. Process 300B continues at operation 312 by querying the user of the digital imaging device when an emission of a specimen is at or near its peak based on the emission profile data to ask the user whether to discontinue capturing images of the specimen. Process 300B further includes operation 313 where a signal for one or more bright bands of emissions from the specimen is calculated based on the ratio of the period of time of exposure taken by the digital imaging device to the total time of the exposure of emissions obtained from the emission profile data. Different weights are assigned to different frames of the series of non-destructive read images based on the emission profile data This completes process 300B according to one example embodiment.

Figure 3C:
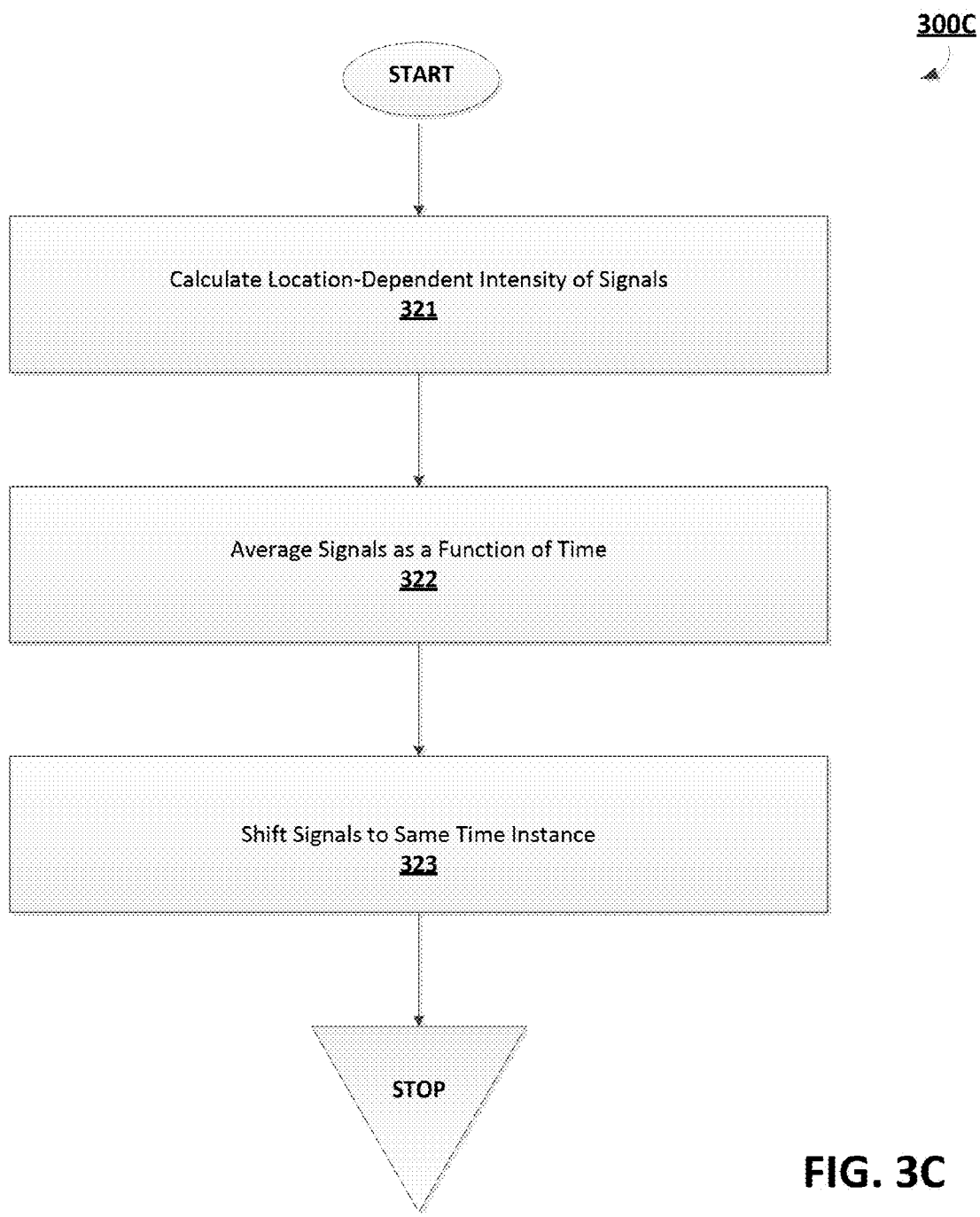
FIG. 3C depicts an example flow chart of a process of using time-based curve fitting to capture an image of a specimen in a chemiluminescence reaction using a series non-destructive read operations according to one embodiment.

FIG. 3C depicts an example flow chart of a process of using time-based curve fitting to capture an image of a specimen in a chemiluminescence reaction using a series non-destructive read operations according to one embodiment. In the illustrated embodiment, process 300C begins at operation 321 by calculating the intensity of each signal read out from the image sensor based on location of the signal in the array of pixels in cases where the time profile of each signal is location dependent. Each signal is then averaged as a function of time to estimate an amount of signal present (operation 322) and the locations of the averaged signals are shifted in time to the same time instance as if each of the signals at each location started simultaneously. In one embodiment, this is done to improve repeatability of the image capture operation. This completes operation 300C according to one example embodiment.

Figure 3D:
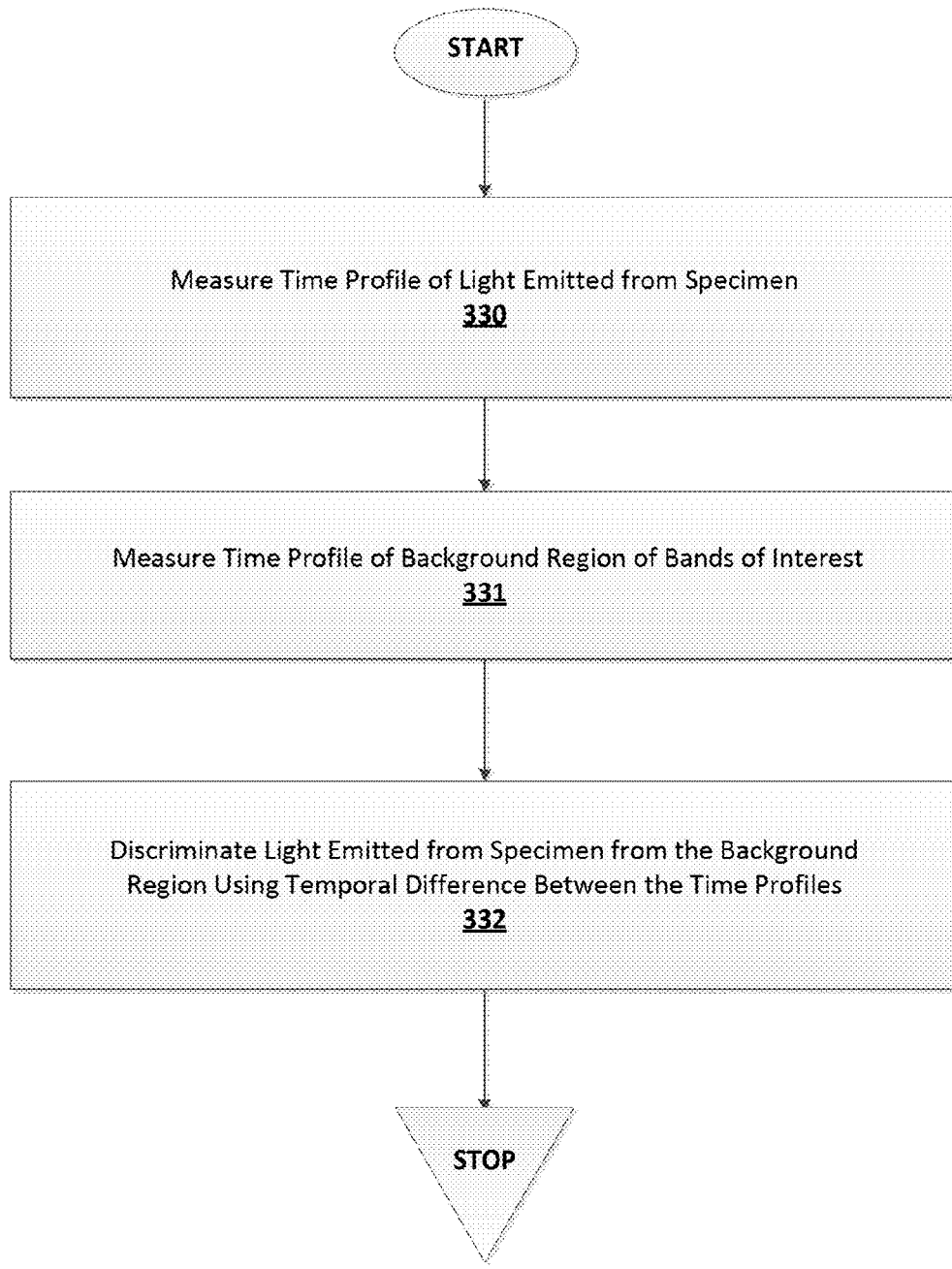
FIG. 3D depicts an example flow chart of a process of using time profile measurements to discriminate light emitted from a specimen from background regions.

FIG. 3D depicts an example flow chart of a process of using time profile measurements to discriminate light emitted from a specimen from background regions according to one embodiment. In the illustrated embodiment, process 300D begins at operation 330 by measuring the time profile of the light emitted from the specimen using the non-destructive read images. Operation 300D continues by measuring the time profile of a background region in proximity to one or more bands of interest in the captured images (operation 331) and discriminating the light emitted from the specimen from the background region using the temporal difference between the measured time profiles to discriminate the signals read out from the image sensor from unwanted background noise (operation 332).

It should be appreciated that the specific operations illustrated in FIGS. 3A-3D provide a particular method of capturing an image of a specimen in a chemiluminescence reaction using a series of non-destructive read operations according to one embodiment. Other sequences of operations may also be performed according to alternative embodiments. For example, alternative embodiments may perform the operations outlined above in a different order and additional operations may be added or removed depending on the particular applications. Moreover, the individual operations may include one or more sub-operations that may be performed in various sequences as appropriate.

FIGS. 4A-4D depict plots of signal intensity verses time for chemiluminescence reactions to illustrate the principles of non-destructive read operations and time profile according to exemplary embodiments. In the illustrated embodiment of FIG. 4A, the signal is integrated only between time instances t1 and t2 for best results. Between times t1 and t2, the signal intensity is strong enough and yet still far enough away from the start of the reaction. Times t1 and t2 can be determined retroactively by analyzing the data that was captured using non-destructive read mode (i.e., taking a series of images). Times t1 and t2 can be determined by the user before or after the experiment. Time t1 can also be zero. An automated algorithm can be used to determine when times t1 and t2 occur, for example by the following methods: (1) when the time-based derivative of the signal reaches a predetermined threshold; or (2) by fitting the time curve to a known model that has predetermined t1 and t2 that are related to parameters in the model such as a time delay parameter, amplitude of the curve etc.

Figure 4A:
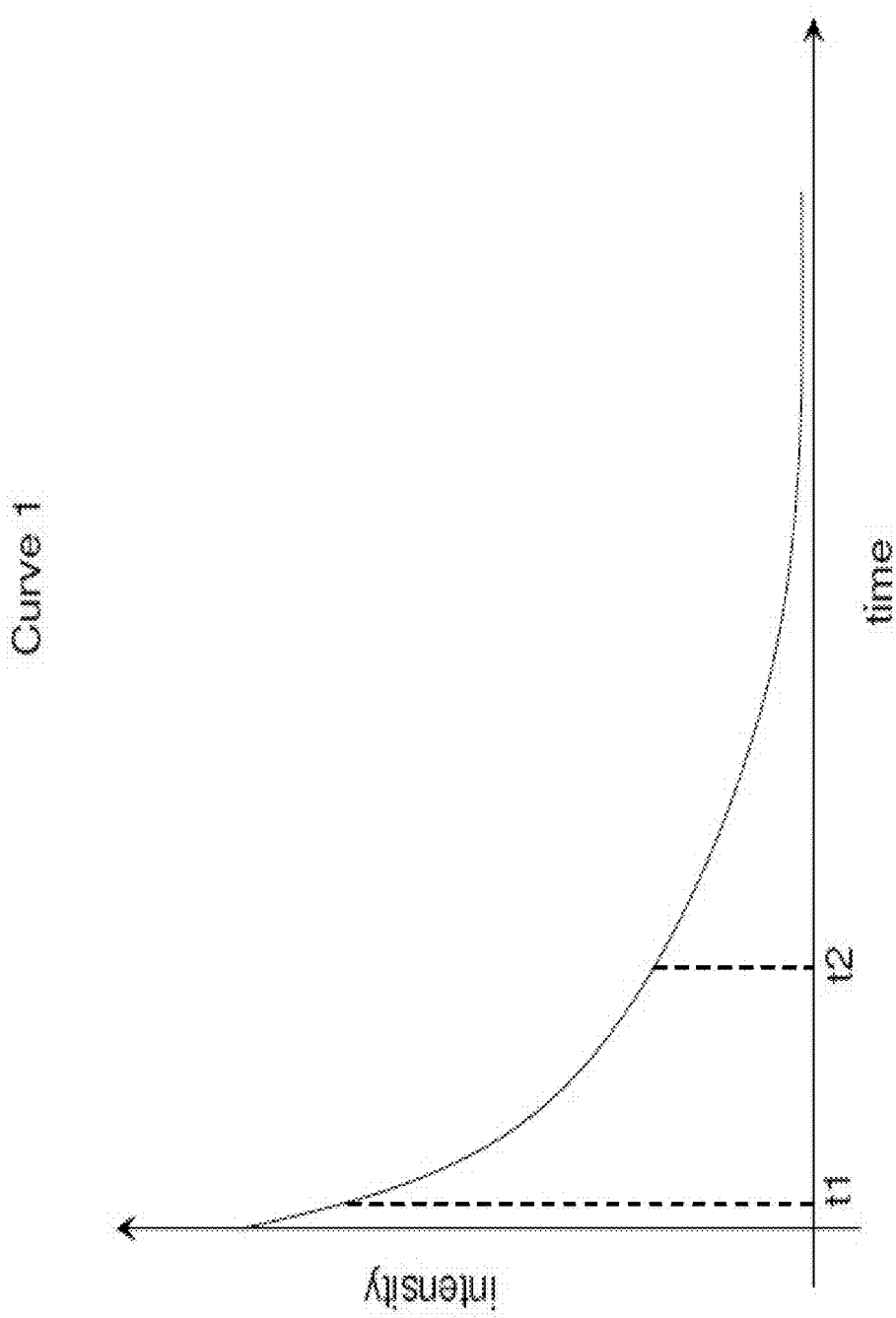
FIG. 4A depicts a plot of signal verses time for a reaction to illustrate the principles of non-destructive read operations and time profile according to exemplary embodiments.
Figure 4B:
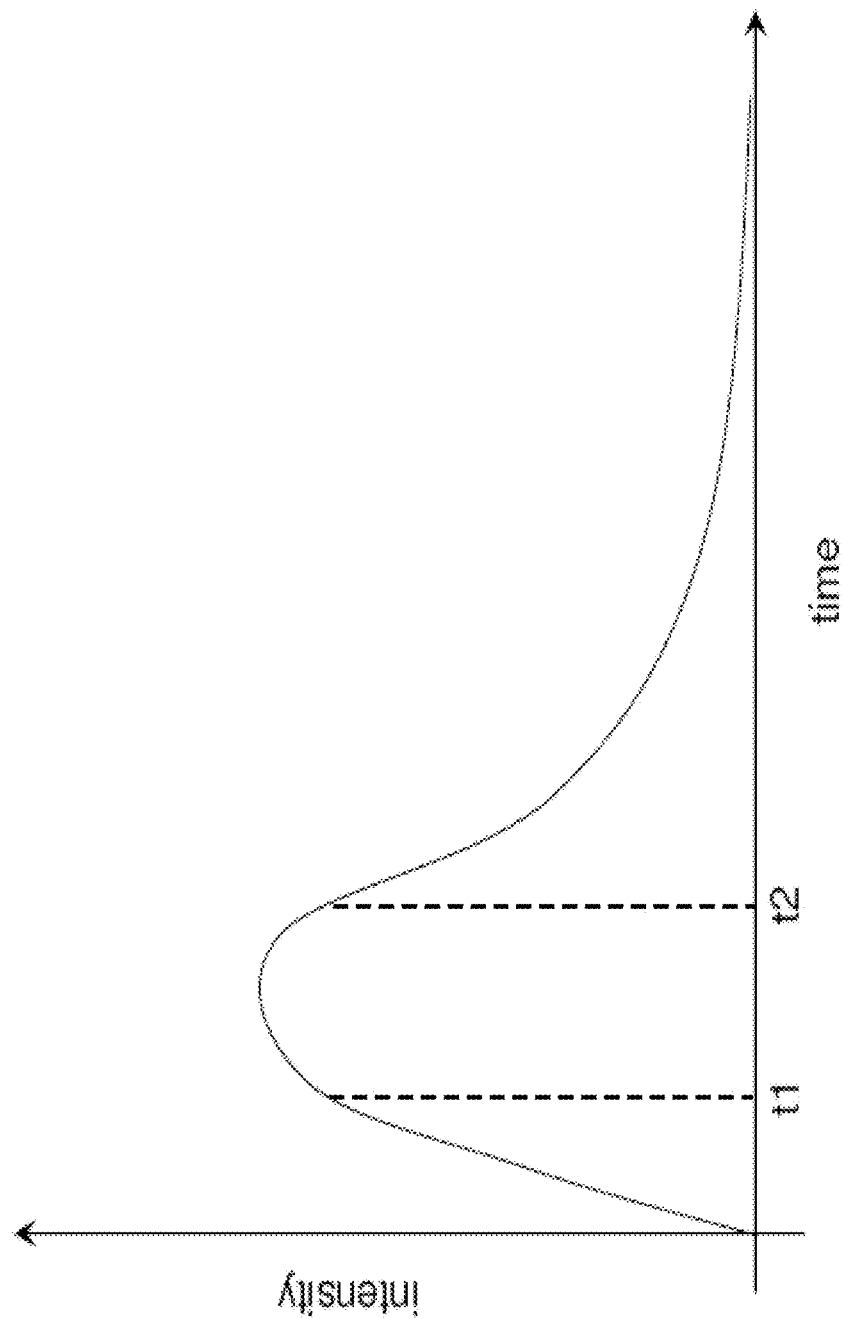
FIG. 4B depicts a plot of signal verses time for a reaction to illustrate the principles of non-destructive read operations and time profile according to exemplary embodiments.

In the illustrated embodiment of FIG. 4B, the signal intensity is integrated only between times t1 and t2 for best results. As can be seen in this case, between times t1 and t2 the signal intensity is higher than the rest of the time curve. Times t1 and t2 can be determined retroactively by analyzing the data that was captured using non-destructive read mode (i.e., taking a series of images). Times t1 and t2 can be determined by the user before or after the experiment. Time t1 can also be zero. An automated algorithm can be used to determine when times t1 and t2 occur, for example by the following methods: (1) when the absolute value of the time-based derivative of the signal is smaller than a predetermined threshold, but is near the peak of the curve where the derivative is approximately zero; or (2) by fitting the time curve to a known model that has predetermined t1 and t2 that are related to parameters in the model such as a time delay parameter, amplitude of curve, etc.

Figure 4C:
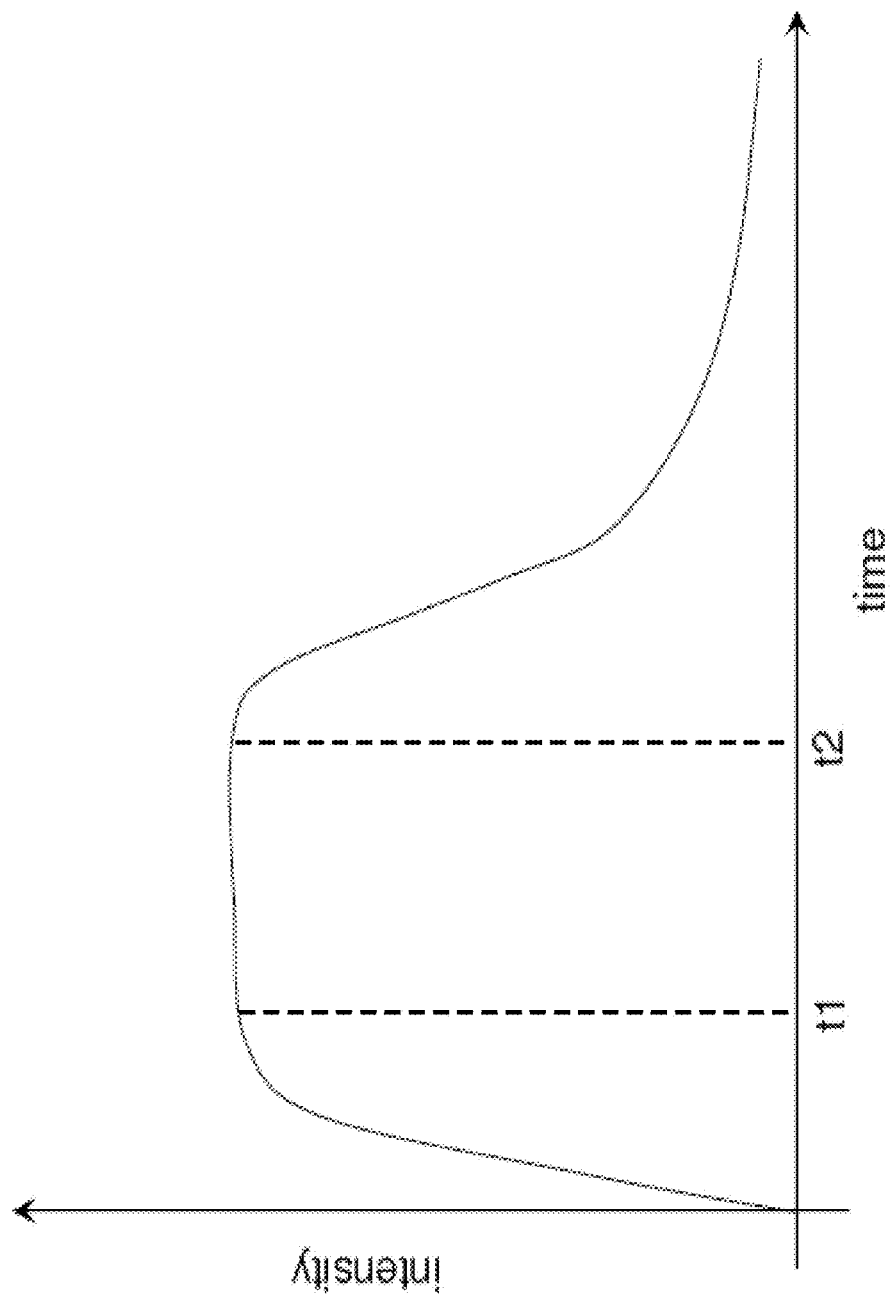
FIG. 4C depicts a plot of signal verses time for a reaction to illustrate the principles of non-destructive read operations and time profile according to exemplary embodiments.

In the illustrated embodiment of FIG. 4C, the signal intensity is integrated only between times t1 and t2 for best results. As can be seen in this case, between times t1 and t2 the signal intensity is approximately constant. Times t1 and t2 can be determined retroactively by analyzing the data that was captured using non-destructive read mode (i.e., taking a series of images). Times t1 and t2 can be determined by the user before or after the experiment. Time t1 can also be zero. An automated algorithm can be used to determine when times t1 and t2 occur, for example by the following methods: (1) when the signal derivative with time is small enough after being large and positive for time values of t<t1, and before being large and negative after time values t>t2 using some threshold; (2) when the signal derivative with time is smaller than some threshold; (3) by fitting the curve to a known model that has predetermined t1 and t2 that are related to parameters in the model such as a time delay parameter, amplitude of the curve, etc.; or (4) the entire signal is integrated numerically, but only the linear part of the integral between t1 and t2 is taken into account (the integral is approximately linear where the curve is approximately constant). Deviation from linearity is determined by thresholds (such as R-squared smaller than some value) or distance of points from a linear fit.

Figure 4D:
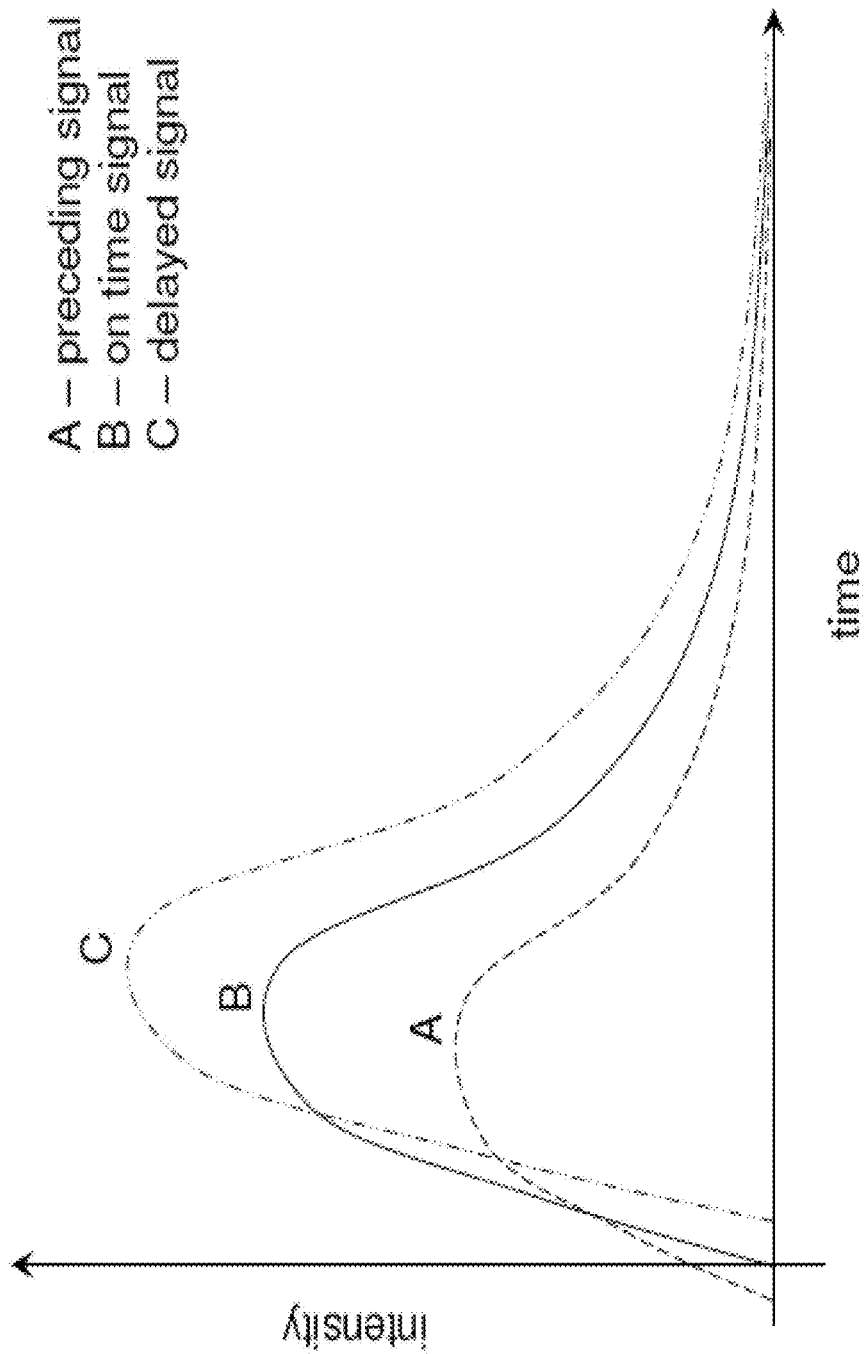
FIG. 4D depicts a plot of signal verses time for a reaction to illustrate the principles of non-destructive read operations and time profile according to exemplary embodiments.

In the illustrated embodiment of FIG. 4D, if for some reason the signal at different bands or areas has a delay in time because of such things as user operations, temperature variations, fluid arrival delay, experiments preformed at different times, or different instruments, then the integration of the signal between predetermined times such as described will reduce signal variation and improve repeatability. This is because with current techniques, only the final integral (sum) of the signal is known. Therefore time delays are not noticeable by the measurement system or user.

Figure 4E:
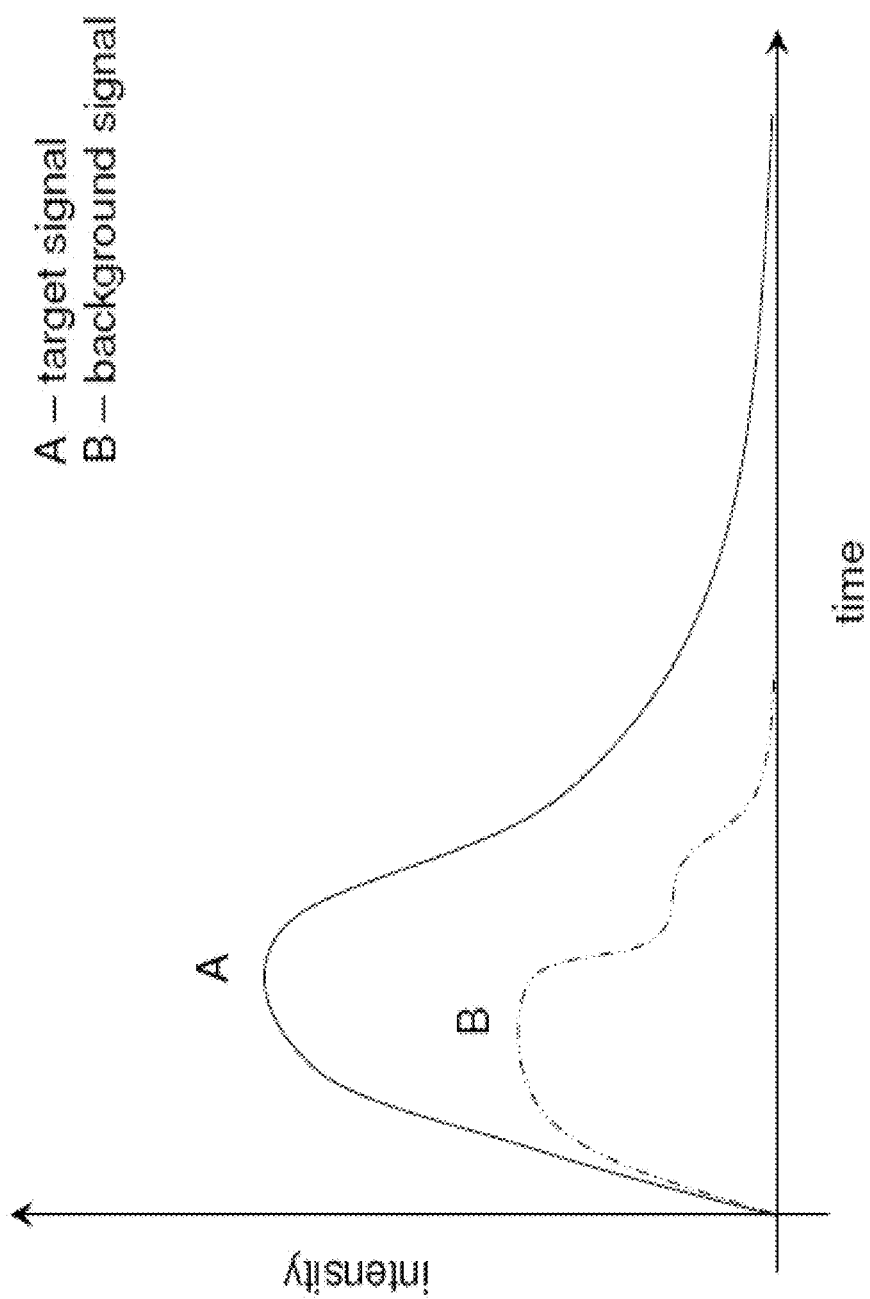
FIG. 4E depicts a plot of signal verses time for a reaction to illustrate the principles of non-destructive read operations and time profile according to exemplary embodiments.

In the illustrated embodiment of FIG. 4E, if the time profile of the signal generated at a background area (because of non-specific binding for example) is different from that of the target signal, then by finding deviations from the known or measured model of the time profile and excluding those unwanted signals can improve SNR and repeatability. Deviation from the model can be found, for example, by setting a threshold on CHI square of a nonlinear curve fit of these curves. With current techniques only the final integral (sum) of the signal is known. Therefore different signal profiles are not noticeable by the measurement system or user, and therefore cannot be excluded as here.

In some embodiments, the specimen is a biological sample, e.g., a protein or nucleic acid (e.g., DNA, RNA, or both) sample. The sample can be bound to a blotting membrane and images of the blotting membranes are determined. Blotting techniques are commonly used in biochemical analyses. For example, mixed samples of biological entities are directly applied to a membrane (e.g., "dot blotting") or applied to electrophoretic gels and the components are separated by application of an electric field across the gel and then applied to a membrane (e.g., Southern, northern, or western blotting). The resulting pattern of migration of the substances contained in the sample is then detected in some manner. Biochemical targets (e.g., a target nucleic acid or protein) are then detected by a probe that binds to the target(s). Exemplary probes include antibodies, other non-antibody proteins, or nucleic acids. In some cases (e.g., when the probe is not directly labeled), the membrane is then treated and incubated with a secondary enzyme-, radioisotope-, fluorfluor-, or biotin- or other label-conjugated antibody specific for the primary probe.

Optionally, a detector reagent, e.g., a chromogenic, chemiluminescent, fluorescent, radiological, or streptavidin-labeled material, is applied which either binds to, or is a substrate of an enzyme linked to the probe, thereby generating a signal. It will be appreciated that there is a wide variety of ways signal from the probe is ultimately generated. Basic texts disclosing the general methods of various blotting techniques include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

In general however, the non-destructive read-out techniques described herein can be applied to various other fields to increase dynamic range and signal-to-noise ratio. For example, slowly changing microscopy objects, (relative to the frame rate) such as cells, could be visualized better using non-destructive read-out operations by averaging many frames (reducing read noise) and increased dynamic range. Plate readers are another example where non-destructive read-out operations can be performed. Further, the cost of many imaging systems that use charge-coupled device ("CCD") image sensors can be reduced by going to CMOS digital imaging devices. The loss in sensitivity of such CMOS devices as compared to CCD devices can be regained by using a non-destructive read-out mode. The non-destructive read-out techniques described herein could also be used in contact imaging microscopy, which is a developing field in the last few years. Other examples of processes that can be used with the techniques described herein are included in Exhibit A.

FIG. 5 depicts an example block diagram of a data processing system upon which the disclosed embodiments may be implemented. Embodiments of the present invention may be practiced with various computer system configurations such as hand-held devices, microprocessor systems, microprocessor-based or programmable user electronics, minicomputers, mainframe computers and the like. The embodiments can also be practiced in distributed computing environments where tasks are performed by remote processing devices that are linked through a wire-based or wireless network. FIG. 5 shows one example of a data processing system, such as data processing system 500, which may be used with the present described embodiments. Note that while FIG. 5 illustrates various components of a data processing system, it is not intended to represent any particular architecture or manner of interconnecting the components as such details are not germane to the techniques described herein. It will also be appreciated that network computers and other data processing systems which have fewer components or perhaps more components may also be used. The data processing system of FIG. 5 may, for example, a personal computer (PC), workstation, tablet, smartphone or other hand-held wireless device, or any device having similar functionality.

As shown, the data processing system 501 includes a system bus 502 which is coupled to a microprocessor 503, a Read-Only Memory (ROM) 507, a volatile Random Access Memory (RAM) 505, as well as other nonvolatile memory 506. In the illustrated embodiment, microprocessor 503 is coupled to cache memory 504. System bus 502 can be adapted to interconnect these various components together and also interconnect components 503, 507, 505, and 506 to a display controller and display device 508, and to peripheral devices such as input/output ("I/O") devices 510. Types of I/O devices can include keyboards, modems, network interfaces, printers, scanners, video cameras, or other devices well known in the art. Typically, I/O devices 510 are coupled to the system bus 502 through I/O controllers 509. In one embodiment the I/O controller 509 includes a Universal Serial Bus ("USB") adapter for controlling USB peripherals or other type of bus adapter.

RAM 505 can be implemented as dynamic RAM ("DRAM") which requires power continually in order to refresh or maintain the data in the memory. The other nonvolatile memory 506 can be a magnetic hard drive, magnetic optical drive, optical drive, DVD RAM, or other type of memory system that maintains data after power is removed from the system. While FIG. 5 shows that nonvolatile memory 506 as a local device coupled with the rest of the components in the data processing system, it will be appreciated by skilled artisans that the described techniques may use a nonvolatile memory remote from the system, such as a network storage device coupled with the data processing system through a network interface such as a modem or Ethernet interface (not shown).

Figure 6:
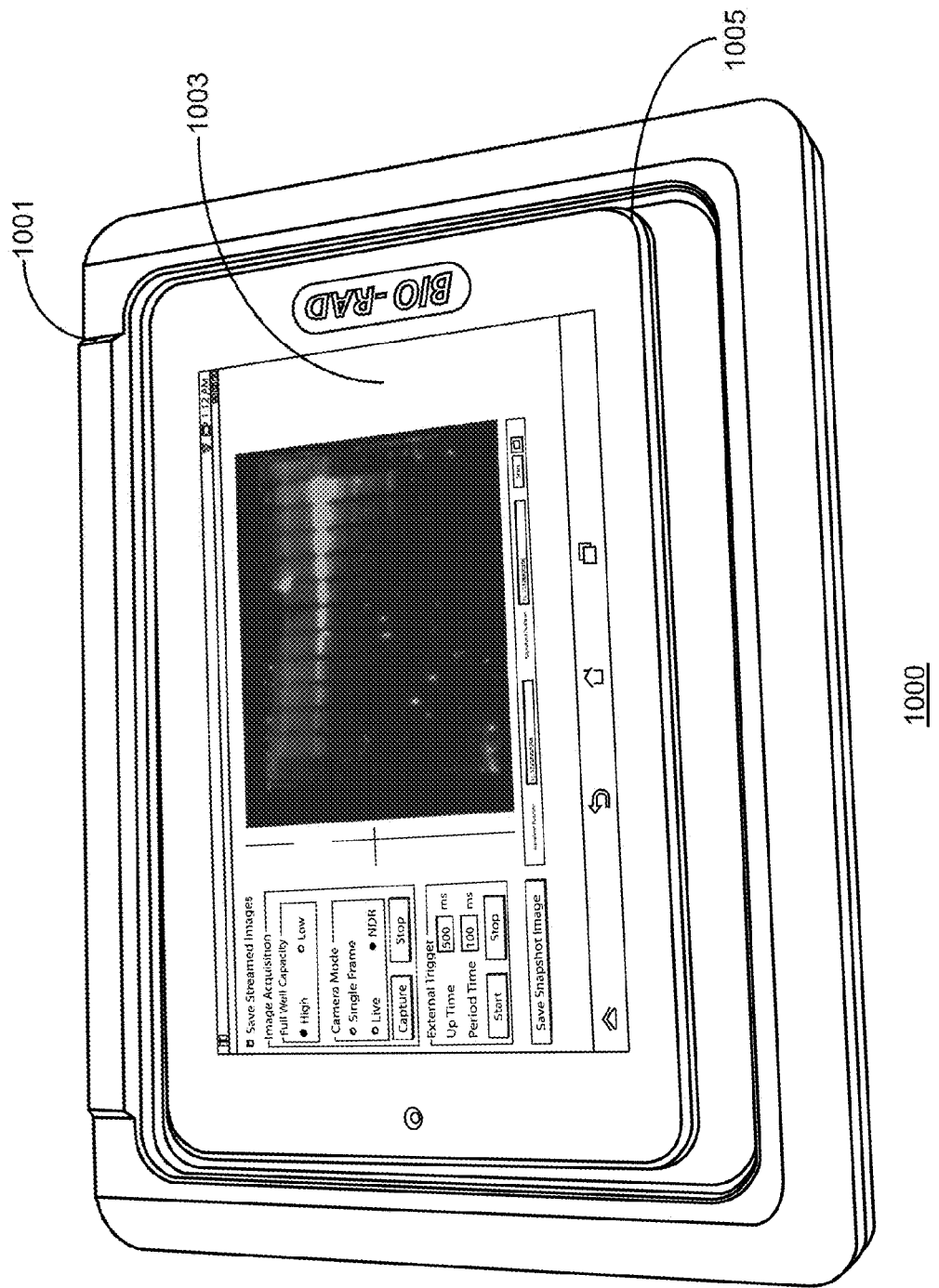
FIG. 6 depicts an exemplary device that can be used in embodiments of the invention.

FIG. 6 shows an exemplary device 1000 that can be used in embodiments of the invention. The device 1000 may be an imaging device. It is understood that this is an exemplary device and that many other devices may be used with embodiments of the invention (e.g., cameras, x-ray machines, etc.). The device 1000 may be used to capture images of light emitted from specimens placed on the device. For example, the device 1000 may comprise a body 1001, a display 1003 (e.g., a touch screen, etc.), and a lid 1005 that rests over a surface area such as a faceplate (e.g., a fiber faceplate) for placing one or more specimens on the device 1000. The faceplate may protect the sensor from a sample or specimen placed on the faceplate. The faceplate may be lightproof, waterproof and easy to clean. A user may lift the lid 1005, place the specimen on the faceplate of the device 1000, and close the lid 1005. The device 1000 may begin to capture images automatically or in response to an indication from the user, such as pushing a button on the display 1003.

As explained above, in some embodiments, the specimen is a biological sample, e.g., a protein or nucleic acid (e.g., DNA, RNA, or both) sample. The sample can be bound to a blotting membrane and images of the blotting membranes comprising labeled probes can be determined. Blotting techniques are commonly used in biochemical analyses. For example, mixed samples of biological entities are directly applied to a membrane (e.g., "dot blotting") or applied to electrophoretic gels and the components are separated by application of an electric field across the gel and then applied to a membrane (e.g., Southern, northern, or western blotting). The resulting pattern of migration of the substances contained in the sample is then detected in some manner. Biochemical targets (e.g., a target nucleic acid or protein) are then detected by a probe that binds to the target(s). Exemplary probes include antibodies, other non-antibody proteins, or nucleic acids. In some cases (e.g., when the probe is not directly labeled), the membrane is then treated and incubated with a secondary enzyme-, radioisotope-, fluorfluor-, or biotin- or other label-conjugated antibody specific for the primary probe.

Optionally, a detector reagent, e.g., a chromogenic, chemiluminescent, fluorescent, radiological, or streptavidin-labeled material, is applied which either binds to, or is a substrate of an enzyme linked to the probe, thereby generating a signal. It will be appreciated that there is a wide variety of ways signal from the probe is ultimately generated. Basic texts disclosing the general methods of various blotting techniques include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

The device 1000 may further comprise an internal power supply and input and output jacks for various components (e.g., a printer, an external computer, an external display, external power supply, etc.). The input and output jacks may be wired or wireless according to known techniques and devices.

The device 1000 may further comprise a sensor (e.g., an image sensor). There are various types of sensors that may be utilized in embodiments of the invention. Some examples of sensor technology include charge coupled device (CCD) or complementary metal oxide semiconductor (CMOS) sensors (e.g., 11×6.9 cm active area, 8.7×13.9 cm, 10.4×15.6 cm, etc.). The sensor may be directly coupled with the faceplate on the device or may be coupled with an imaging system and the imaging system may be coupled with the faceplate. The sensor may comprise an array of pixels. In embodiments of the invention the array of pixels may be a two-dimensional array or a linear or one-dimensional array.

The device may further comprise a processor coupled with the sensor. The processor of the device may be configured to perform various processes associated with the device. For example, the processor may be configured to capture a series of short exposures of light emissions from the specimen over a period of time during the reaction, wherein captured images of the specimen grow dynamically over the period of time as the number of exposures increases, wherein the series of short exposures is captured using an array of pixels of an image sensor of a digital imaging device configured to perform continuous non-destructive read operations to read out a set of signals representing non-destructive read images of the specimen from the array of pixels of the image sensor, and wherein reading out the set of signals is delayed until the end of the period of time to reduce read noise in the set of non-destructive read images, monitor the set of signals read out from the image sensor, and discontinue capturing images of the specimen upon receiving a command, wherein the command is generated automatically or is based on input from a user of the digital imaging device.

With these embodiments in mind, it will be apparent from this description that aspects of the described techniques may be embodied, at least in part, in software, hardware, firmware, or any combination thereof. It should also be understood that embodiments can employ various computer-implemented functions involving data stored in a data processing system. That is, the techniques may be carried out in a computer or other data processing system in response executing sequences of instructions stored in memory. In various embodiments, hardwired circuitry may be used independently, or in combination with software instructions, to implement these techniques. For instance, the described functionality may be performed by specific hardware components containing hardwired logic for performing operations, or by any combination of custom hardware components and programmed computer components. The techniques described herein are not limited to any specific combination of hardware circuitry and software.

Embodiments herein may also be in the form of computer code stored on a computer-readable medium. Computer-readable media can also be adapted to store computer instructions, which when executed by a computer or other data processing system, such as data processing system 500, are adapted to cause the system to perform operations according to the techniques described herein. Computer-readable media can include any mechanism that stores information in a form accessible by a data processing device such as a computer, network device, tablet, smartphone, or any device having similar functionality. Examples of computer-readable media include any type of tangible article of manufacture capable of storing information thereon such as a hard drive, floppy disk, DVD, CD-ROM, magnetic-optical disk, ROM, RAM, EPROM, EEPROM, flash memory and equivalents thereto, a magnetic or optical card, or any type of media suitable for storing electronic data. Computer-readable media can also be distributed over a network-coupled computer system, which can be stored or executed in a distributed fashion.

Throughout the foregoing description, for the purposes of explanation, numerous specific details were set forth in order to provide a thorough understanding of the invention. It will be apparent, however, to persons skilled in the art that these embodiments may be practiced without some of these specific details. Accordingly, the scope and spirit of the invention should be judged in terms of the claims which follow as well as the legal equivalents thereof.

What is claimed is:

1. A method of capturing digital images of a specimen in a chemical reaction comprising:
    capturing, by an imaging device, a series of short exposures of light emissions from the specimen over a period of time during the reaction, wherein captured images of the specimen grow dynamically over the period of time as the number of exposures increases, wherein the series of short exposures is captured using an array of pixels of an image sensor of a digital imaging device configured to perform continuous non-destructive read operations to read out a set of signals representing non-destructive read images of the specimen from the array of pixels of the image sensor, and wherein reading out the final set of signals is delayed until the end of the period of time to reduce read noise in the set of non-destructive read images;
    monitoring, by the imaging device, the sets of signals representing the non-destructive read images read out from the image sensor;
    discontinuing capturing images of the specimen, by the imaging device, upon receiving a command, wherein the command is generated based on the monitored signals; and
    increasing a dynamic range of the captured images of the specimen by combining data from shorter-time read images of the set of non-destructive read images for brighter areas of the specimen with data from longer-time read images of the set of non-destructive read images for dimmer areas of the specimen.

2. The method of claim 1 further comprising displaying the captured images of the specimen in a graphical display.

3. The method of claim 1 wherein the digital imaging device comprises a complementary metal-oxide-semiconductor ("CMOS") digital imaging device capable of performing non-destructive read operations.

4. The method of claim 3 wherein images captured using the CMOS digital imaging device exhibit minimal blooming due to over-saturation from bright pixels, and wherein long exposures of bright bands of light emitted from the specimen are performed even if the bright bands are located in proximity to faint bands emitted from the specimen.

5. The method of claim 1 further comprising:
storing in a memory of the digital imaging device emission profile data of multiple different assays including information relating to when an emission for a particular assay will begin rapidly declining; and
selecting the end of the period of time based at least in part on the emission profile of the particular assay.

6. The method of claim 5 further comprising:
expanding bit depth of the captured images; and
calculating a signal for one or more bright bands of emissions from the specimen based on a ratio of the period of time of exposure of emissions from the specimen taken by the digital imaging device to a total time of the exposure of emissions from the specimen obtained from the emission profile data.

7. The method of claim 5 wherein the emission profile data is either known beforehand or measured by a user of the digital imaging device.

8. The method of claim 5 further comprising using the emission profile data to improve auto-exposure of the particular specimen.

9. The method of claim 5 further comprising querying the user of the digital imaging device when an emission of a specimen is at or near its peak based on the emission profile data to ask the user whether to discontinue capturing images of the specimen.

10. The method of claim 5 wherein different weights are assigned to different frames of the series of non-destructive read images based on the emission profile data.

11. The method of claim 1, further comprising:
capturing images of the specimen at a high frame rate using the non-destructive read operations; and
averaging frames captured at the end of the period of time to reduce read noise.

12. The method of claim 1 further comprising averaging or applying curve fitting methods of each signal read out from the image sensor as a function of time to estimate an amount of signal present to increase sensitivity of the image sensor in the digital imaging device.

13. The method of claim 1 further comprising:
calculating an intensity of each signal read out from the image sensor based on location of the signal in the array of pixels, wherein a time profile of each signal is location dependent;
averaging each signal as a function of time to estimate an amount of signal present; and
shifting locations of the averaged signals to a same time instance as if each of the signals at each location started simultaneously.

14. The method of claim 1 wherein the reaction is a chemiluminescence reaction, a fluorescence reaction, or an absorbance reaction.

15. The method of claim 1 further comprising:
measuring a first time profile of the light emitted from the specimen using the non-destructive read images;
measuring a second time profile of a background region close to one or more bands of interest in the captured images; and
discriminating the light emitted from the specimen from the background of the images using a temporal difference between the first and second time profiles to discriminate the signals read out from the image sensor from unwanted background noise.

16. The method of claim 1 further comprising:
utilizing black pixels in a background region in proximity to a band of interest in the captured images to measure dark current noise for each exposure; and
eliminating local offsets and gain variations arising from temperature variations based on the dark current noise measurements.

17. The method of claim 16 further comprising improving fixed pattern dark noise reduction within the captured images based on the dark current noise measurements.

18. A digital imaging device for capturing digital images of a specimen in a chemical reaction comprising:
a processor;
a memory coupled with the processor via an interconnect bus;
an image sensor comprising an array of pixels for capturing a series of short exposures of light emissions from the specimen over a period of time during the reaction, wherein captured images of the specimen grow dynamically over the period of time as the number of exposures increases,
wherein the image sensor is configured to perform continuous non-destructive read operations to read out a set of signals representing non-destructive read images of the specimen from the array of pixels, and wherein the final reading out the signals is delayed until the end of the period of time to reduce read noise in the set of non-destructive read images; and
a monitoring module configured to continuously monitor the signals representing the non-destructive read images read out from the image sensor and discontinue capturing images of the specimen based on the monitored signals;
wherein the digital imaging device is further configured to increase a dynamic range of the captured images of the specimen by combining data from shorter-time read images of the set of non-destructive read images for brighter areas of the specimen with data from longer-time read images of the set of non-destructive read images for dimmer areas of the specimen.

19. The digital imaging device of claim 18 further comprising a graphical display configured to display the captured images of the specimen.

* * * * *